United States Patent
Perkins

(10) Patent No.: US 6,605,253 B1
(45) Date of Patent: Aug. 12, 2003

(54) INTERVENTION TECHNIQUES FOR REDUCING CARCASS CONTAMINATION

(75) Inventor: Michael Perkins, Poquoson, VA (US)

(73) Assignee: Zentox Corporation, Boston, MA (US)

( * ) Notice: Subject to any disclaimer, the term of this patent is extended or adjusted under 35 U.S.C. 154(b) by 237 days.

(21) Appl. No.: 09/591,513

(22) Filed: Jun. 9, 2000

Related U.S. Application Data

(60) Provisional application No. 60/138,368, filed on Jun. 10, 1999.

(51) Int. Cl.[7] .............. A61L 9/00; B01J 19/08; C02F 1/76; B01D 1/00; A21D 4/00
(52) U.S. Cl. .............. 422/28; 422/31; 422/32; 422/34; 422/37; 422/79; 422/186.07; 210/752; 210/756; 210/760; 210/704; 210/724; 210/905; 426/320; 426/321; 426/326; 426/332; 426/335
(58) Field of Search .............. 422/1, 6, 28–37, 422/38, 41, 79, 101, 119, 121, 123, 186.07, 186.1, 186.12, 186.21, 256, 261, 292, 301, 305–307; 210/752, 754, 756, 760, 764, 704, 905, 724–725; 426/320–321, 326, 332, 335

(56) References Cited

U.S. PATENT DOCUMENTS

| | | | |
|---|---|---|---|
| 3,314,880 A | 4/1967 | Rubin | 210/44 |
| 3,350,301 A | 10/1967 | Hoffman | 210/44 |
| 3,732,163 A | 5/1973 | Lapidot | 210/47 |
| 3,912,533 A | 10/1975 | Heyer | 127/13 |
| 3,945,918 A | 3/1976 | Kirk | 210/44 |

(List continued on next page.)

FOREIGN PATENT DOCUMENTS

| | | |
|---|---|---|
| EP | 0 331 296 A1 | 9/1989 |
| EP | 0 353 314 A1 | 2/1990 |
| EP | 0 468 461 A1 | 1/1992 |

OTHER PUBLICATIONS

"Preozonation as a Coagulant Aid in Drinking Water Treatment", Saunier, Selleck and Trussell, Journal AWWA, May 1983, pp. 239–246.

"Ozone as a Coagulant Aid", Reckhow, Singer, Trussell, AWWA Seminar Proceedings No. 20005, 1986, pp. 17–46.

*Primary Examiner*—Robert J. Warden, Sr.
*Assistant Examiner*—Monzer R. Chorbaji
(74) *Attorney, Agent, or Firm*—John C. Serio; Brown Rudnick Berlack Israels LLP

(57) ABSTRACT

The presently disclosed disinfection process for use in the processing of foodstuffs is designed as an intervention step in poultry processing to allow for continuous on-line processing of poultry carcasses that may have accidentally become contaminated during the evisceration process. Such on-line processing is designed to replace the need for off-line manual washing and cleaning of the contaminated carcasses. By eliminating such off-line manual washing, food safety will be enhanced due to the elimination of the physical handling of carcasses and the cross-contamination that may result from such physical handling. An additional benefit is that the production process will also be able to run with a reduced number of interruptions, which will result in a more efficient production process. The invention described herein is designed to employ the advantages of controlled chlorination at optimum pH levels, together with the proven effectiveness of increased contact time through the implementation of multiple stage treatment of the carcasses during slaughter, evisceration, washing and chilling. Additionally, an improved device and method are provided for effecting economic and efficient regulation of disinfection agent effectiveness, comprising a system and method for removing a major portion of filterable materials, represented as total chemical oxidation demand from the chiller tank water.

15 Claims, 4 Drawing Sheets

U.S. PATENT DOCUMENTS

| | | | |
|---|---|---|---|
| 3,951,795 A | 4/1976 | Doncer et al. ................. 210/61 |
| 4,021,585 A | 5/1977 | Svoboda et al. ............ 426/332 |
| 4,277,334 A | 7/1981 | Ruidisch et al. ............ 210/632 |
| 4,309,388 A | 1/1982 | Tenney et al. .............. 210/154 |
| 4,481,080 A | 11/1984 | Mallon ....................... 422/304 |
| 4,517,159 A | 5/1985 | Karlson ....................... 422/20 |
| 4,608,165 A | 8/1986 | Galper ....................... 210/232 |
| 4,744,903 A | 5/1988 | McAninch et al. ......... 210/632 |
| 4,744,904 A | 5/1988 | McAninch et al. ......... 210/632 |
| 4,790,943 A * | 12/1988 | Dunn et al. |
| 4,827,727 A | 5/1989 | Caracciolo ..................... 62/63 |
| 4,844,189 A | 7/1989 | Shisgal et al. ............... 177/211 |
| 4,849,237 A | 7/1989 | Hurst ......................... 426/332 |
| 4,868,950 A | 9/1989 | Harben, Jr. ................... 17/11.2 |
| 4,876,004 A | 10/1989 | Verhoeff ...................... 210/170 |
| 4,947,518 A | 8/1990 | Covell, III ................... 17/11.2 |
| 5,053,140 A * | 10/1991 | Hurst |
| 5,132,010 A | 7/1992 | Ossenkop ................... 210/121 |
| 5,173,190 A | 12/1992 | Picek ......................... 210/651 |
| 5,178,755 A | 1/1993 | LaCrosse ................. 210/195.1 |
| 5,227,184 A | 7/1993 | Hurst ......................... 426/312 |
| 5,248,439 A | 9/1993 | Derrell ....................... 210/708 |
| 5,593,598 A | 1/1997 | McGinness et al. ........ 210/748 |
| 5,728,305 A | 3/1998 | Hawkinson ................. 210/760 |
| 5,759,415 A | 6/1998 | Adams ....................... 210/776 |
| 5,882,253 A * | 3/1999 | Mostoller |

* cited by examiner

INTERVENTION TECHNIQUES FOR REDUCING CARCASS CONTAMINATION

CROSS-REFERENCE TO RELATED APPLICATIONS

This Patent Application claims the benefit of U.S. Provisional Application No. 60/138,368 filed Jun. 10, 1999, the contents of which are incorporated herein by reference in its entirety.

BACKGROUND

1. Technical Field

The present disclosure relates generally to the field of carcass processing, and particularly, is directed to an enhanced water disinfection process for use in the processing of a foodstuffs. More particularly, the disinfection process is designed as an intervention step in poultry processing to allow for continuous on-line processing of poultry carcasses that may have accidentally become contaminated during the evisceration process.

2. Background of the Related Art

The typical poultry processing plant receives live animals from the grow-out farms, slaughters the animals, drains the blood and then removes the feathers, "paws", heads and eviscera in the initial stages of processing. The carcasses are thereafter sent by way of mechanized line operations through a series of washing, chilling and sanitizing steps before the product is shipped as "fresh" product or packaged for freezing. These line operations typically consume large quantities of water.

Accordingly, the poultry processing industry has generally been characterized as a large volume consumer of water in conducting the slaughter, processing, and packing of the animals for both human consumption and other uses. Recent initiatives by the United States Department of Agriculture (USDA), under the jurisdiction of the Food Safety Inspection Service (FSIS), have resulted in a further increase in the volume of water used to wash poultry carcasses in order to meet the more stringent requirements of zero (0) tolerance for visible fecal contamination. Furthermore, recent introduction of Hazardous Analysis and Critical Control Point (HACCP) programs provide for the transition of the inspection process from one heavily weighted by USDA oversight to a more self-regulated format wherein the poultry producer shoulders more of the inspection burden. As a consequence, there has been additional heightened awareness and recognition of the need for greater product safety, including the reduction of microbial contamination levels.

The poultry industry has been actively seeking intervention methods designed to meet the current USDA regulations for continuous on-line processing. These regulations deal with the corrective actions that are mandated to remove carcasses that have been contaminated during evisceration with digestive tract materials. The regulations require that these contaminated carcasses be removed from the main processing line and transferred to an approved reprocessing line where the contamination can be removed by washing, trimming, vacuuming or a combination of these steps.

Prior method disinfection and processing goals have been to act as an intervention step which allows for the continuous on-line processing of poultry carcasses using a single point treatment which utilizes either trisodium phosphate washing or acidified chlorite. In general, single point treatment of a rapidly moving carcass on a production line is insufficient to meet the complex food safety requirements in a poultry processing plant. The single point treatment system using trisodium phosphate washing is described in U.S. Pat. No. 5,882,253. In the case of trisodium phosphate, the process is further disadvantaged by the introduction to the plant's operations of increased levels of nutrients such as phosphates (i.e;, a byproduct of trisodium phosphate) that may need to be removed in the plant's wastewater operations due to environmental discharge regulations or concerns.

Such environmental discharge regulations and concerns require that poultry processing plants decrease the level of nutrients such as phosphates in wastewater discharge. Additionally, the application of trisodium phosphate elevates the pH of the carcass being processed, as well as the process water all of which carries over to the plant's chill system. The increased pH level in the chill system makes downstream chlorine disinfection less effective without significant chemical additions.

As discussed above and as dictated by the state of the art poultry or carcass processing plants, the current processes fail to appreciate the benefits associated with pH control, multiple point controlled treatment, or even the unexpected advantages to be gained by reducing the organic loads within such process water. By failing to appreciate these requirements, the conventional approaches commonly suffer from difficult treatment challenges and as a result, these approaches have been accompanied by disadvantageously high operating costs and reduced efficiency. This has in turn translated in to reduced product quality and reduced processing plant productivity.

SUMMARY

The various objects and aspects of the present invention are met using an approach which focuses on appropriately regulating and controlling the pH of the process water to be disinfected and through addition, regulation and control of a disinfecting agent. The control of pH and level of disinfecting agent is implemented throughout multiple steps in the production process including any process water to be recovered and reused. This is in contrast to prior approaches which have failed to appreciate the benefits associated with pH control, multiple point controlled treatment, or even the unexpected advantages to be gained by reducing the organic loads within such process water.

Advantages of the present invention comprise processes which allow for the automated regulation of the pH of poultry processing water, preferably at certain stages of the process, so as to dramatically improve the efficiency and effectiveness of antimicrobial or other disinfection agents added. The poultry process treatment water which can especially benefit includes the water used in poultry scalding, picking, post-pick washing, evisceration, carcass washing and other stages of poultry processing designed to physically remove any fecal matter, ingesta and other digestive tract remnants from the slaughter and evisceration processes. Additionally, an improved device and method are provided for effecting economic and efficient regulation of disinfection agent and control of the disinfection chemistry throughout the multiple steps of the production process.

Physical removal of visible fecal material and other contaminants from poultry carcasses will be carried out by serial carcass washing steps (e.g., scalder, picker, post pick spray wash, inside/outside carcass washing cabinets and outside carcass washing cabinets) where medium pressure, high volume water spraying is employed. The introduction of USDA approved antimicrobial agents (e.g., calcium hypochlorite or others), applied at optimum pH control level for chlorine disinfection at multiple treatment stages (e.g., scalder, picker, post pick spray wash, inside/outside carcass wash and outside carcass wash) and using the best practical control methods is designed to significantly reduce microbial levels on all carcasses prior to and after their entry into the submersion chiller system.

The invention described herein is designed to employ the advantages of controlled chlorination (e.g., calcium hypochlorite and/or other USDA approved food grade biocides) at optimum pH levels, together with the proven effectiveness of increased contact time (CT) through the implementation of multiple stage treatment of the carcass during slaughter, evisceration, washing and chilling.

Additionally, an improved device and method are provided for effecting economic and efficient regulation of disinfection agent effectiveness comprising a system and method for removing a major portion of filterable materials including fats, oils and greases (FOG), total suspended solids (TSS), proteins, blood products, lipids and other materials represented as total is chemical oxidation demand (COD) from the chiller tank water.

The presently disclosed disinfection process for use in the processing of foodstuffs is designed as an intervention step in poultry processing to allow for continuous on-line processing of poultry carcasses that may have accidentally become contaminated during the evisceration process. Such on-line processing is designed to replace the need for off-line manual washing and cleaning of the contaminated carcasses. By eliminating such off-line manual washing, food safety will be enhanced due to the elimination of the physical handling of carcasses and the cross-contamination that may result from such physical handling. An additional benefit is that it will be possible to run the production process with a reduced number of interruptions, which will result in a more efficient production process. The disinfection process according to the present invention, include: the removal, using the processing plant's existing washing, spraying and mechanical scrubbing devices (modified if required), of visible fecal material or other contaminants from the carcasses resulting from the mechanical evisceration process; the introduction of an enhanced antimicrobial treatment agent at multiple stages to improve food safety by reduction of total microbial levels; the improvement of disinfection in the facility's overall production process including the carcass chiller system through the use of pH controlled chlorination to further reduce microbial counts, and the reduction of the amount of physical handling of carcasses and therefore, reduction of the potential for cross-contamination.

Further, the present invention is specifically designed to be easily incorporated into the processor's existing production equipment and plant layout. This ease of implementation is accomplished by using, to the greatest extent possible, the processor's existing carcass wash stations, scalders, pickers and other designated treatment points as the point of treatment by using the existing water piping and delivery systems as the means of delivery of the invention's chemical and disinfection enhancements.

The invention described herein is designed to meet the current USDA regulations for removal of visible fecal material using the plant's existing washing, spraying and mechanical scrubbing devices, and to reduce microorganism counts and improve food safety, all in a more cost effective and environmentally friendly manner than other approaches.

An additional benefit of the invention relates to those poultry processors who have or who intend to implement water reuse programs. Such water reuse programs, as is the subject of U.S. application Ser. No. 09/507,163, filed Feb. 18, 2000 and which is hereby incorporated by reference in its entirety, have met with favorable and advantageous results by returning reuse water that has been disinfected with ozone and then chlorinated at an advantageous dosage before being reintroduced to the production process at an upstream point, such as in the scalder or similar heating portion of the processing steps. The reintroduction of the chlorinated reuse water into the scalder or similar heating processing step causes a dramatic reduction in the levels of microorganisms associated with the carcasses that have not been found in the prior art. Also, it is an embodiment of the present disclosure, to introduce chlorinated and/or ozonated water (or other approved disinfectant) along the foodstuffs processing steps, particularly along the points where the use of heated water is applicable, such as in the scalder or similar processing steps which subject the carcasses to heated water. In such heated processing steps, the pores and tissue membranes of the carcasses are open and are more readily receiving of the surrounding water, i.e., the chlorinated and/or ozonated water, thereby having greater efficacy to the removal of microorganisms associated with such foodstuff processing.

In view of the foregoing, the advantages of the present disclosure include providing new methods for improving the effectiveness of the disinfection agent being used, new methods for improving the decontamination of poultry or other foodstuff and the water used in the processing of said poultry and other foodstuff, and water reuse methods which cause a reduction in the levels of microorganisms associated with the carcasses.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may best be understood by reference to the following description, taken in connection with the accompanying drawings, in which:

DETAILED DESCRIPTION OF PREFERRED EMBODIMENTS

Figure 1:
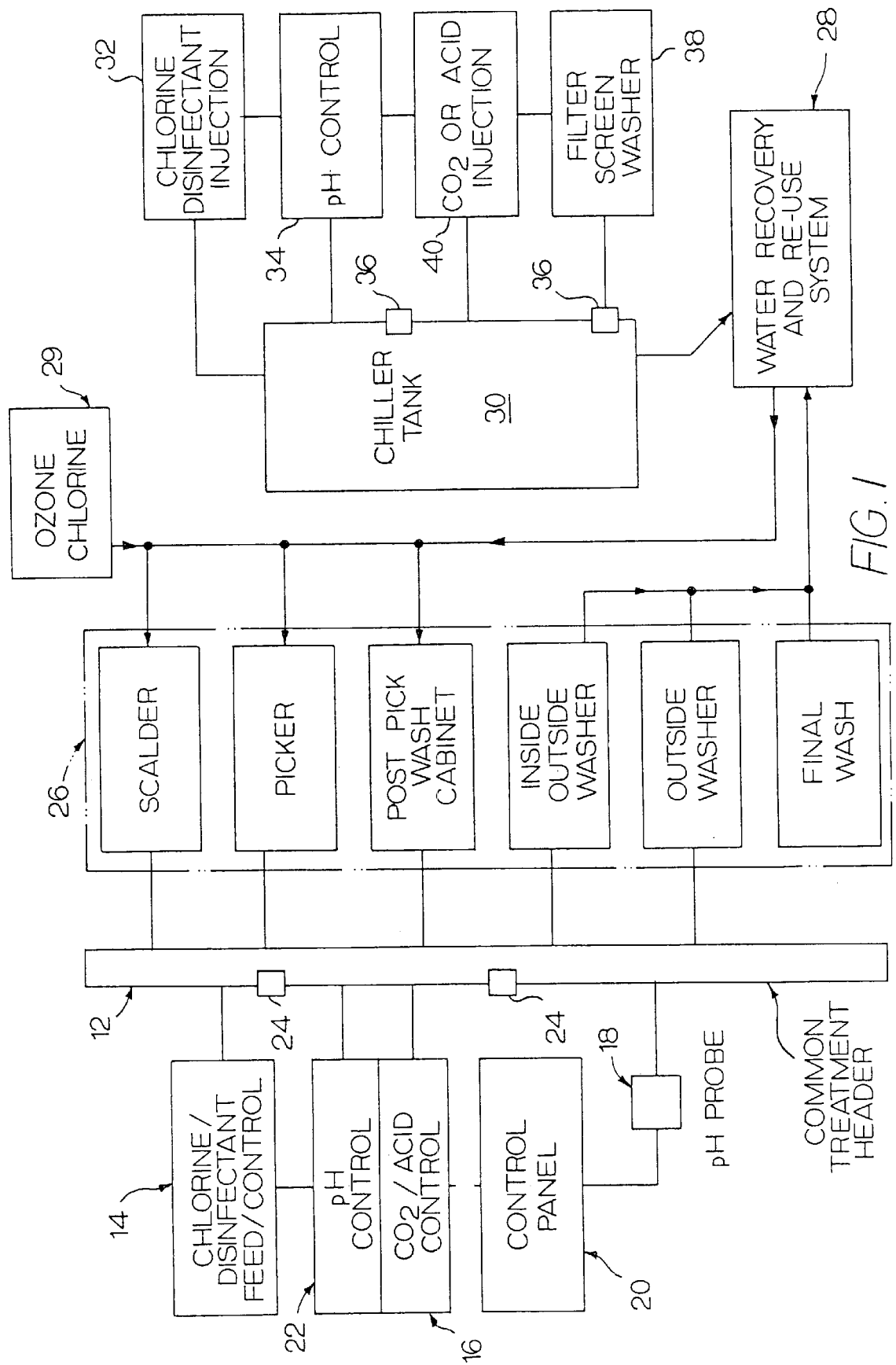
FIG. 1 depicts a flow chart of the multi-stage chlorination process and chiller treatment system according to the present disclosure.

The preferred embodiments of the apparatus and methods disclosed herein are discussed in terms of a disinfection process designed as an intervention step in poultry processing to allow for continuous on-line processing of poultry carcasses that may have accidentally become contaminated during the evisceration process. It is envisioned, however, that the disclosure is applicable to a wide variety of processes including, but not limited to, general carcass or foodstuffs processing including processing operations used in poultry, beef and pork slaughter plants.

As discussed throughout the present disclosure, the control of the pH of the treatment water within product processing water optimizes the elimination of pathogens and other microorganisms. Also, by providing an intervention step to allow for continuous on-line processing of poultry carcasses, there is a reduction in the amount of physical handling of carcasses and therefore, a reduction in the potential for cross-contamination of the carcasses, thereby improving quality and food safety. The present disclosure also discloses methods and devices for improving the effectiveness of disinfection agents in chiller tank processing water by substantial removal of filterable materials. A particular advantage is the fact that the methods of the present invention can be "retrofitted" to existing processing plants without any significant alteration of the plant's "footprint" or layout.

While the processes and devices described will be equally applicable to the aqueous processing of a variety of foodstuffs, for convenience, the application to the poultry processing industry will be described. This industry uses significant volumes of water in its processing operations. Much of the water used during such processing is regulated by the USDA, although the quantity and process steps vary from plant to plant. On average, the typical slaughter plant will use between 5 and 15 gallons per animal, divided into several key elements:

The Scalding process—USDA guidelines dictate a minimum of 1 quart per animal.

The Picking (de-feathering) process—varies from plant to plant.

The Evisceration process—varies from plant to plant.

Carcass washing (including Inside/Outside Carcass Washers, Intermediate Wash Stations and Final Rinse Cabinets)—these combined carcass wash steps can use between 2 and 6 gallons per animal.

The Chilling process (chillers)—USDA guidelines require minimum overflow rates of 0.5 gallons per animal in whole bird chiller tanks and temperature control. Various processors also utilize chilled water for "paws", gizzards and other edible organs sold commercially. Typical chiller operations can consume between 0.75 and 1.5 gallons per animal.

Plant Sanitation—plant sanitation can use between 1.5 and 3 gallons per animal.

Equipment wash—a typical processing plant will use between 0.25 and 1 gallon per animal in equipment washing (this is an "on-line" process and should be differentiated from sanitation during which the entire plant and equipment is washed and sanitized when the plant is not in production).

Miscellaneous water usage—truck wash, live loading shed wash, domestic water, wastewater and industrial (non-product contact uses such as evaporative cooling for refrigeration, vacuum pump seal and cooling and compressor cooling) wash.

Most of the water is used during the evisceration and carcass washing steps and is typically applied by mechanical mechanisms comprising spray washing devices, cabinet type washers, brush washers and medium and/or high-pressure water spraying heads. The present invention takes advantage of the use of these existing water processing steps and mechanisms in improving the disinfection of the processing water and thus the processed foodstuff thereby improving its quality and safety.

Figure 2A:
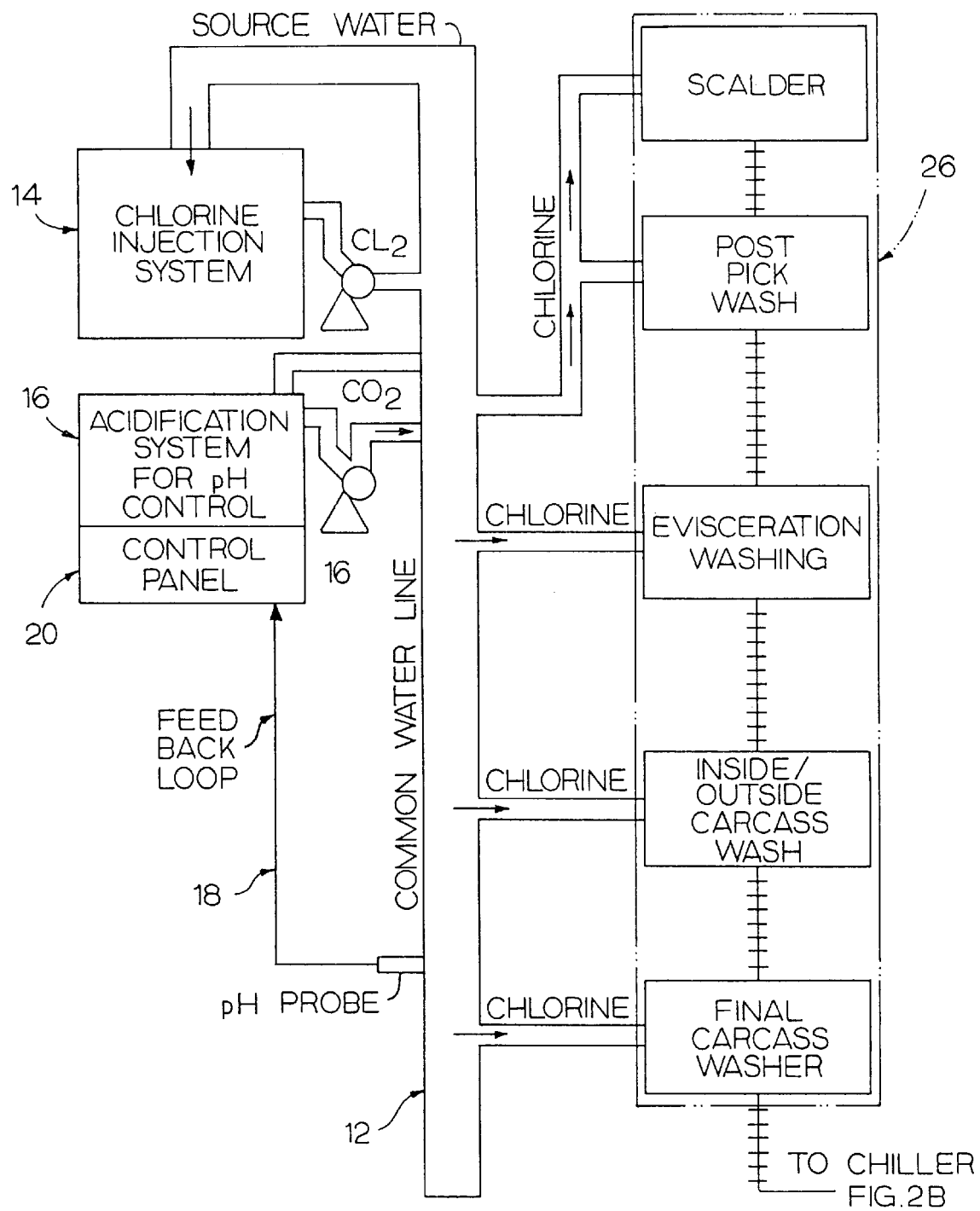
FIG. 2A provides a more detailed flow plan of the multi-stage chlorination process of FIG. 1.
Figure 2B:
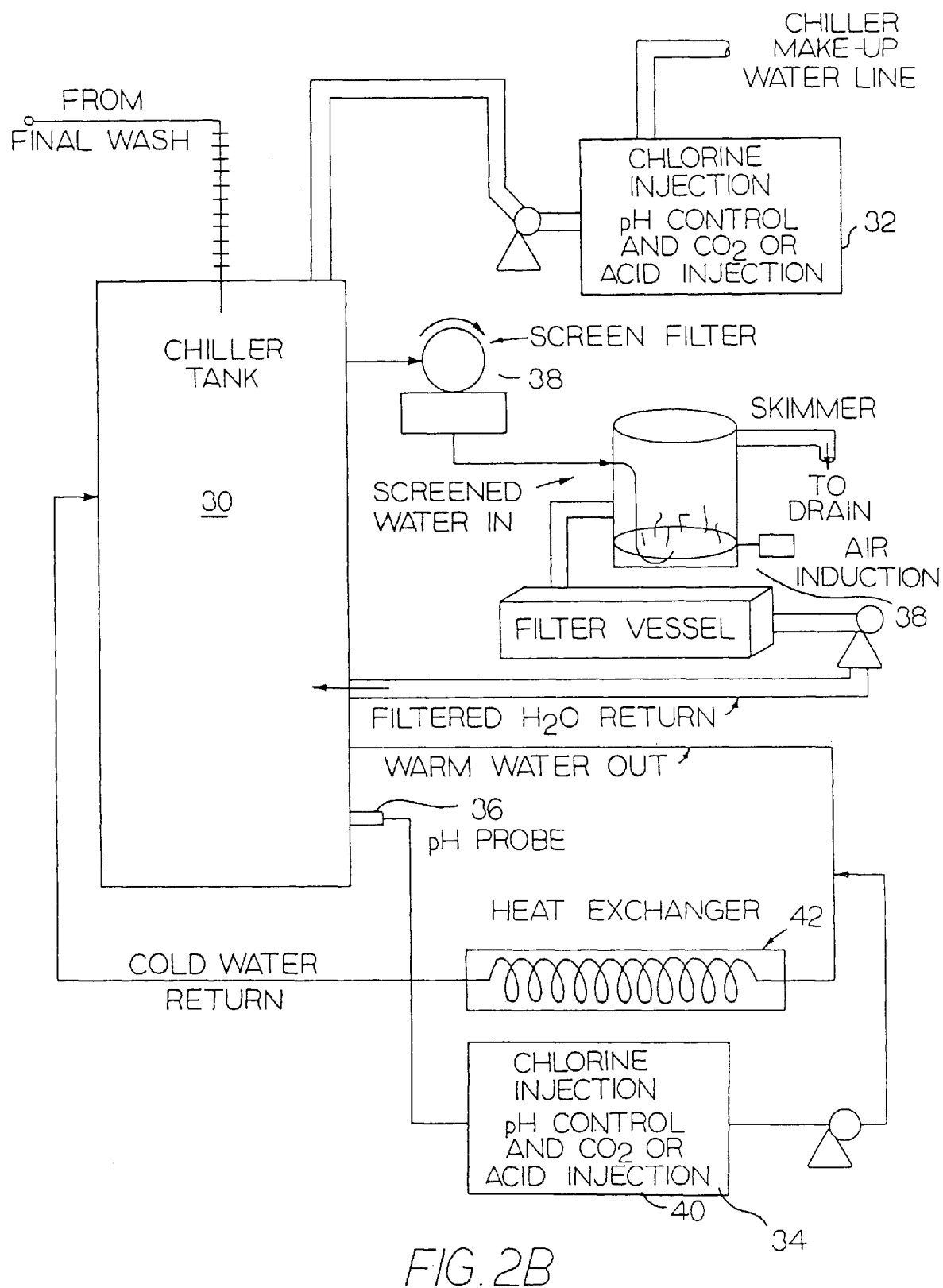
FIG. 2B provides a more detailed flow plan of the chiller treatment system of FIG. 1.

Referring to FIGS. 1, 2A and 2B, the physical aspects of the present disclosure are illustrated as a common header 12 (either existing in the processing plant or, modification of the plant's water delivery system or, a custom, site built common header) used as the delivery mechanism to convey the treated water (e.g., calcium hypochlorite plus pH control) to the designated treatment points in the process. A tablet or liquid chlorine feed system 14 sized to deliver the maximum practical and allowable dosage of chlorine to the entire volume of water required to serve the multiple stages of treatment is situated along the common header 12. Also situated is a gas/liquid or, liquid/liquid injection device 16 to permit the introduction of the preferred acidification agent (e.g., $CO_2$, or other chemical agent) into the water in the delivery header to alter the levels of pH in the treatment water based on the readings of the pH probe 18. A control panel 20 is used along the process in order to monitor the readings and control the dosages of the chemical agents required to perform the disinfection and pH control 22. Multiple sensors 24 are located along the common header 12 in order to monitor, control the conveyance of the enhanced disinfection chemistry, measure chlorine levels and pH levels and send via electronic signal (feedback loops) the measurements to the proper chemical controllers.

The present disclosure makes use of (with or, without modifications) the plant's existing carcass wash cabinets and mechanical washing devices 26 to assist in the removal of visible contamination and serve as treatment points for the delivery of the enhanced disinfection chemistry. Devices for scalding, feather picking, post-pick washing and evisceration line washing stations act as additional treatment points for the delivery of the enhanced disinfection chemistry, as well as the plant's water recycle and reuse system 28, where the water has been disinfected with ozone (ozonated) or other appropriate disinfectant and then dosed with an appropriate level of an approved disinfection agent (e.g., calcium hypochlorite or others) before being reintroduced into the production process at an upstream point, such as in the scalder or similar heating portion of the processing steps. An alternative to the disclosed water recovery and reuse system 28 is an ozonating or chlorinating system 29 which simply ozonates or chlorinates outside water and reintroduces such water to any or all of the heated processing steps, i.e. the scalder step, the picker step and the post-pick step, which utilize heated water (heated water being defined as water used during poultry processing which is or was heated at some point, preferably, but not limited to, at the scalder step). This reintroduction, like with the water recovery and reuse system 28, reduces the levels of contamination within the poultry.

Multi-Stage, Controlled pH Chlorination During Poultry Processing

While the USDA mandates the use of a disinfection agent (typically chlorine) at various stages of the poultry processing operations, it is silent concerning the conditions under which the as disinfection agent is employed. It has been discovered that the effectiveness of the disinfection agent may be dramatically altered by characteristics of the processing water being treated, most notably pH, but also by the solute load presented by filterable materials. Other aspects of the present invention lie in the ability to improve the disinfection quality of the processing water at multiple points during processing. This becomes important because the effectiveness of a disinfection agent is directly proportional to the time in which the microorganisms to be killed are in contact therewith. The importance of contact time has been reflected in the US Environmental Protection Agency's (USEPA) Contact Time "CT" Values, in its guidelines concerning the disinfection of drinking water. These relationships have been perhaps most clearly spelled out by a mathematical formula developed by Chick in 1908, which described the kinetics of disinfection:

$$N_t = N_0 \exp(-kt)$$

Where:

$N_t$=number of microorganisms surviving after time t $N_0$=initial number of microorganisms −k=rate constant dependent upon type of microorganism and disinfectant t=time the organisms is in contact with the disinfectant USEPA CT Values are expressed as mg/L-min; where mg/L=concentration of disinfectant min=time in contact with disinfectant Clearly then, the longer and/or more often that the microorganisms (whether in the water or on the poultry being processed) come into contact with the disinfectant, the greater the reduction of microorganisms and the safer the poultry.

However, it has been discovered that there are still other factors which must be considered, including those which affect the efficacy of the disinfection agent. Several of the embodiments of the present invention take advantage of methods of optimizing these factors, chief amongst which is pH. The temperature and pH level of the water into which the disinfection agent, e.g. chlorine, is introduced can dramatically affect the effectiveness of the disinfection agent. This is illustrated by Tables 1–7 shown below, which are published by the USEPA concerning guidelines to CT values (lower numbers mean higher antimicrobial efficacy) in drinking water. These tables show the dramatic improvement in effectiveness of chlorine and chlorine derivatives at both lower pH and higher temperature. The tables also demonstrate how different microorganisms react differently to disinfection agents, e.g., viruses require longer contact periods to be inactivated.

The methods of the present invention capitalize upon these effects by adjusting the pH of the processing water to levels between pH 5 and 8, most preferably between pH 6.5 and 7, and by bringing such pH controlled disinfecting water into contact with the carcasses at multiple processing points. While the level of hypochlorous acid will continue to increase as pH levels continue to decline (thereby resulting in greater anti-microbial activity), the resulting corrosive nature of liquids with severely depressed pH can have deleterious effects upon plant equipment, not to mention hazard to equipment operators and hence, such reduced pH levels do not represent the optimum practical levels. The inverse of this is also true.

TABLE 1

CT Values for 3-log (99.9%) Inactivation of Giardia Cysts By Free Chlorine at Water Temperature 10.0° C. (50° F.)

| Free Residual | pH | | | | | | |
|---|---|---|---|---|---|---|---|
| mg/L | ≦6.0 | 6.5 | 7.0 | 7.5 | 8.0 | 8.5 | ≦9.0 |
| ≦0.4 | 73 | 88 | 104 | 125 | 149 | 177 | 209 |
| 0.6 | 75 | 90 | 107 | 128 | 153 | 183 | 218 |
| 0.8 | 78 | 92 | 110 | 131 | 158 | 189 | 226 |
| 1.0 | 79 | 94 | 112 | 134 | 162 | 195 | 234 |
| 1.2 | 80 | 95 | 114 | 137 | 168 | 200 | 240 |
| 1.4 | 82 | 98 | 116 | 140 | 170 | 206 | 247 |
| 1.6 | 83 | 99 | 119 | 144 | 174 | 211 | 253 |
| 1.8 | 88 | 101 | 122 | 147 | 179 | 215 | 259 |
| 2.0 | 87 | 104 | 124 | 150 | 182 | 221 | 265 |
| 2.2 | 89 | 105 | 127 | 153 | 186 | 225 | 271 |
| 2.4 | 90 | 107 | 129 | 157 | 190 | 230 | 276 |
| 2.6 | 92 | 110 | 131 | 160 | 194 | 234 | 281 |
| 2.8 | 93 | 111 | 134 | 163 | 197 | 239 | 287 |
| 3.0 | 95 | 113 | 137 | 166 | 201 | 243 | 292 |

TABLE 2

CT Values for Inactivation of Viruses By Free Chlorine Log Inactivation

| Temperature, ° C. | 2.0-log pH 6–9 | pH 10 | 3.0-log pH 6–9 | pH 10 | 4.0-log pH 6–9 | pH 10 |
|---|---|---|---|---|---|---|
| 0.5 | 6 | 45 | 9 | 66 | 12 | 90 |
| 5 | 4 | 30 | 6 | 44 | 8 | 60 |
| 10 | 3 | 22 | 4 | 33 | 6 | 45 |
| 15 | 2 | 15 | 3 | 22 | 4 | 30 |
| 20 | 1 | 11 | 2 | 16 | 3 | 22 |
| 25 | 1 | 7 | 1 | 11 | 2 | 15 |

Note: CT values can be adjusted to other temperatures by doubling the CT for each 10° C. drop in temperature.

TABLE 3

CT Values for Inactivation of Giardia Cysts By Chloramine Within the pH Range 6 to 9 Temperature, ° C.

| Inactivation | ≦1 | 5 | 10 | 15 | 20 | 25 |
|---|---|---|---|---|---|---|
| 0.5–log | 635 | 365 | 310 | 250 | 185 | 125 |
| 1–log | 1270 | 735 | 615 | 500 | 370 | 250 |
| 1.5–log | 1900 | 1100 | 930 | 750 | 550 | 375 |
| 2–log | 2535 | 1470 | 1230 | 1000 | 735 | 500 |
| 2.5–log | 3170 | 1830 | 1540 | 1250 | 915 | 625 |
| 3–log | 3800 | 2200 | 1850 | 1500 | 1100 | 750 |

TABLE 4

CT Values for Inactivation of Viruses By Chloramine* Temperature, ° C.

| Inactivation | ≦1 | 5 | 10 | 15 | 20 | 25 |
|---|---|---|---|---|---|---|
| 2-log | 1243 | 857 | 643 | 428 | 321 | 214 |
| 3-log | 2063 | 1423 | 1067 | 712 | 534 | 356 |
| 4-log | 2883 | 1988 | 1491 | 994 | 746 | 497 |

*This table applies for systems using combined chlorine where chlorine is added prior to ammonia in the treatment sequence.

TABLE 5

CT Values for Inactivation of Giardia Cysts By Chlorine Dioxide Within the pH Range 6 to 9 Temperature, ° C.

| Inactivation | ≦1 | 5 | 10 | 15 | 20 | 25 |
|---|---|---|---|---|---|---|
| 0.5-log | 10 | 4.3 | 4.0 | 3.2 | 2.5 | 2.0 |
| 1-log | 21 | 8.7 | 7.7 | 6.3 | 5.0 | 3.7 |
| 1.5-log | 32 | 13.0 | 12.0 | 10.0 | 7.5 | 5.5 |
| 2-log | 42 | 17.0 | 15.0 | 13.0 | 10.0 | 7.3 |
| 2.5-log | 52 | 22.0 | 19.0 | 16.0 | 13.0 | 9.0 |
| 3-log | 63 | 26.0 | 23.0 | 19.0 | 15.0 | 11.0 |

TABLE 6

CT Values for Inactivation of Giardia Cysts By Chloride Dioxide Within the pH Range 6 to 9 Temperature, ° C.

| Inactivation | ≦1 | 5 | 10 | 15 | 20 | 25 |
|---|---|---|---|---|---|---|
| 0.5-log | 10 | 4.3 | 4.0 | 3.2 | 2.5 | 2.0 |
| 1-log | 21 | 8.7 | 7.7 | 6.3 | 5.0 | 3.7 |
| 1.5-log | 32 | 13.0 | 12.0 | 10.0 | 7.5 | 5.5 |
| 2-log | 42 | 17.0 | 15.0 | 13.0 | 10.0 | 7.3 |

TABLE 6-continued

CT Values for Inactivation of Giardia Cysts By Chloride Dioxide
Within the pH Range 6 to 9
Temperature, ° C.

| Inactivation | $\leq 1$ | 5 | 10 | 15 | 20 | 25 |
|---|---|---|---|---|---|---|
| 2.5-log | 52 | 22.0 | 19.0 | 16.0 | 13.0 | 9.0 |
| 3-log | 63 | 26.0 | 23.0 | 19.0 | 15.0 | 11.0 |

TABLE 7

CT Values for Inactivation of Viruses by Chorine Dioxide
Within the pH Range 6 to 9
Temperature, ° C.

| Inactivation | $\leq 1$ | 5 | 10 | 15 | 20 | 25 |
|---|---|---|---|---|---|---|
| 2-log | 8.4 | 5.6 | 4.2 | 2.8 | 2.1 | 1.4 |
| 3-log | 25.6 | 17.1 | 12.8 | 8.6 | 6.4 | 4.3 |
| 4-log | 50.1 | 33.4 | 25.1 | 16.7 | 12.5 | 8.4 |

Accordingly, the preferred methods of the present invention incorporate the introduction of chlorine, a chlorine derivative (a preferred disinfectant agent), ozone or other approved disinfectant at a controlled pH (adjusted appropriately for the disinfectant employed given the additional practical considerations previously described). The introduction of such disinfectant in a combined system of chlorine injection (or mixing) and acidification (using carbon dioxide, citric acid, lactic acid or any other acid compound (s) approved for contact with food products by the USDA) into solution of the feed water is used in the following processing stages: the Scalders, the Pickers, the Post pick washers, the Inside Carcass Washers, the Inside/Outside Carcass Washers, the Outside Carcass Washers, the Final Carcass Washers and any other practical stage where water is used to physically remove contamination.

Similarly, disinfection of the foodstuffs are realized from the production of "chloramines" during the "up stream" introduction of the treated reuse water into processes employing elevated water temperatures. According to the present disclosure, the water reuse system incorporated in a poultry processing plant does not remove significant levels of nitrogen or ammonia from the process water which, subsequent to the ozonating step, combines with added chlorine passing through the cascade process, i.e., the gathering of process water from a number of source points in the production line, thereby forming various "chloramines" which, in the environment of elevated temperatures, aides in the reduction of microorganisms in the foodstuffs.

The processes of the present invention take advantage of frequent surface and internal contact of the disinfectant with the carcass to increase microorganism lethality and the disinfectant remaining on the carcass external surface and internal surfaces to allow for additional time between the various process stages. Therefore, by beginning the treatment or disinfection process at earlier stages of poultry carcass processing, many advantages are realized.

First, introducing disinfectant at earlier stages results in inactivation (kill) of additional potentially pathogenic organisms not addressed in the current practices. The carcass will be at a higher temperature directly after the scalder stage and into the "post pick" stage. Higher carcass temperatures result in opening of the pores on the carcass skin and loosening of the skin from the muscle tissue. At these conditions, the disinfectant will contact surfaces and tissues that later become unavailable (e.g. closed) as the carcass temperature falls (especially in the chiller tanks).

Second, introduction of disinfectant during evisceration, the disinfectant will contact the surfaces of the carcass at the stage when potential contamination with fecal material or ingesta is most likely. Additionally, some residual disinfectant will be carried over to the next stage allowing for additional contact time.

Third, carcass washing with water treated with disinfectant, whether carried out in one stage or in multiple stages (various processors utilize different methods, washer designs and frequency of washers), will again allow for additional surface contact with the disinfectant at its highest efficiency (due to controlled pH).

Lastly, the entire process at these stages is also designed to reduce the contaminant (microorganism) load as the carcass is sent to the chillers. Any reduction in the organic loading prior to the carcass entry into the chiller tank will serve to reduce the risk of cross-contamination when the carcasses are immersed in a common tank (communal bath).

The following chart reflects an example of time "t" value potentials using Multi-Stage Chlorination (at controlled pH) during poultry processing:

| | Stage | Direct Contact Time | Time Between Stages | Cumulative Time "t" |
|---|---|---|---|---|
| 1. | Scalders | 60–120 seconds | 5–20 seconds | 65–140 seconds |
| 2. | Pickers | 30–90 seconds | 6–9 seconds | 36–99 seconds |
| 3. | Post Pick Wash | 5–15 seconds | 5–10 seconds | 10–25 seconds |
| 4. | IOBW Wash | 10–30 seconds | 6–16 seconds | 16–46 seconds |
| 5. | Final wash | 10–30 seconds | 8–18 seconds | 18–48 seconds |
| | Total Time | | | 2.4–6.0 minutes |

Enhanced Disinfection of Carcasses in Poultry Chiller Tanks

In an alternative embodiment, there is incorporated some of the same disinfection enhancements, as previously described, i.e., introduction of the disinfectant at pH levels where the maximum "active" compound is present in the poultry chiller tanks. Current practices and USDA guidelines require chiller tanks to be monitored for chlorine residual or total chlorine. The concentrations and testing protocols required vary from plant to plant. Generally because there are no specific mandates for disinfection of chiller tanks, there tends to be no uniformity in approach. The processes of the present invention benefit from utilization of an equipment package designed to continuously monitor and adjust the introduction of acidification to control pH level in the chiller tank as to allow for the maximum potential effective formation of hypochlorous acid (in those circumstances where chlorine is used) to enhance the disinfection process.

Similar practical considerations apply with respect to heat and the disinfection process. The invention is advantageously designed to utilize the elevation in water temperature at the scalding stage of the slaughter process. In poultry scalders, as well as the poultry picker and post-pick steps, the temperature of the water (and hence the poultry contained therein) is elevated to between 140 degrees F. and 170 degrees F. At these temperatures, the animal's skin releases from the muscle tissue and allows the aqueous chlorination to contact a larger surface area of the carcass. Also, the elevated temperature results in a higher reaction rate of chlorine reaction. Accordingly, the methods of the present invention, which provide controlled dosing of a disinfection agent, ideally will apply beginning with those processing steps which follow the initial slaughter steps.

With reference to FIGS. 2A and 2B, an advantage of the present invention includes the employment of a chiller tank water quality enhancement process. This process is ideally designed to continuously remove "filterable materials" from the chiller tank including FOG, TSS and COD. Disinfection is commonly affected by an oxidation process where the oxidant (e.g., hypochlorous acid, hypobromous acid, chlorine dioxide, ozone, hydrogen peroxide etc.) is the active disinfection agent. Since the oxidative reaction by the oxidation agent in water is a non-preferential one, the presence of high organic loading will pose a correspondingly higher oxidant demand to achieve comparable inactivation of microorganisms. To improve efficiency, the present inventive methods remove organics such as FOG, TSS and COD from the water to permit use of a lower disinfectant dosage to achieve the desired disinfection standard or "kill efficiency."

These methods can ideally be practiced with the preferred devices of the present invention which comprise mechanism(s) for continuous "mass load" organic removal. This is ideally accomplished by the use of mass removal by floatation, screening or other suitable means, followed by fine filtration using Diatomaceous Earth (DE) filters, membranes or other suitable methods of removing the identified "filterable" materials. It has been discovered that this will enhance the chiller tank's water quality, reduce significantly the disinfectant demand and greatly increase the efficiency of employing disinfection at this critical stage of the process.

The ideal process utilizes an equipment package designed to continuously monitor and adjust the introduction of acidification to control pH in the chiller tanks, and allows for the maximum potential effective formation of hypochlorous acid (where chlorine is used) to enhance the disinfection process. As previously described, the chiller water treatment equipment consists of similar equipment packages.

Using the USEPA CT values, this stage represents the highest potential for disinfection enhancement. This is due to the length of time the carcass is immersed in the chiller bath (typically between 1.5 and 3.0 hours). Assuming a disinfectant dosage that will result in 5.0 ppm "free residual", the resulting CT credit equates to 450–900 mg/L-min.

While the description of the present invention focuses on the use of some form of chlorine as the disinfection agent, it is important to note that other disinfection agents may be advantageously applied at one or more steps in the process. Disinfection agents such as chlorine dioxide, ozone, chlorites, etc., may be used to increase the effectiveness of the process.

In addition, the methods for improving disinfection processes may be advantageously combined with improved methods of water recovery and re-use within the processing plant (see, for example, U.S. application Ser. No. 09/507,163, filed Feb. 18, 2000, and previously made part of this disclosure by incorporation). Under such an approach, process water will be taken from the processing operations, filtered and disinfected to levels determined by the USDA. In such a system and following filtration, the filtered water is pumped by a centrifugal, end suction, top discharge pump to a disinfection system. Disinfection of the water is accomplished by the introduction of gaseous ozone into the filtered water. Ozone is generated by a corona discharge type ozone machine using cryogenic oxygen or, oxygen separated by pressure swing adsorption on-site as the parent gas. The ozone is preferably introduced into the filtered water by way of a venturi type gas/liquid mixing device (Mazzei Injector). The ozonated water is pumped through a pressure dwell manifold or a high efficiency, centrifugal gas/liquid-mixing device to promote maximum dissolution of the ozone gas. The ozonated water flows to an ozone contact tank (304 stainless steel) ideally sized to achieve a minimum of about 7 to 10 minutes of contact time. Ozone generator sizing is based on USEPA criteria for 3 to 4-log removal efficiency at an applied dose of a maximum of 7 ppm and a standard of 5 ppm. The ozone contact tank is fitted with either a dissolved ozone measuring device or an Oxidation-Reduction Potential (ORP) probe. This probe is interfaced with the dissolved ozone monitor or the ORP monitor in the system's main control panel, and dissolved ozone level or ORP is constantly displayed on the panel front. ORP and/or dissolved ozone is ideally controlled to achieve the desired disinfection standard determined by microbiological analysis at various dissolved ozone or ORP set points to assure that the water is pathogen free. A 750-mv set point is commonly used to indicate the sterility of water. The International Bottled Water Association (IBWA) and others indicate that, at this level of oxidation, the water is deemed sterile by drinking water standards and that microbiological activity is eliminated. An alarm is activated if ORP falls below the programmed setpoint and the system can be shut down. Following disinfection by ozonation, the water is rechlorinated at an advantageous dosage before being returned to the scalder or other heating processing steps.

As can be seen from FIGS. 1 and 2B, the apparatus for employing the embodiments of the enhanced disinfection of carcasses in poultry chiller tanks 30 includes the following primary components: the disinfectant distribution system 32, pH control system 34 including acid control 40, on-line monitoring 36, organic mass removal system 38 (filtration for chiller tanks), a water reuse system 28, and/or an ozonating or chlorinating system 29.

The disinfectant distribution system 32 is designed to introduce, through direct injection into the process stream, the desired disinfectant. This sub-component may be advantageously configured for liquid/liquid injection and mixing, gas/liquid injection and/or solid dissolution followed by liquid/liquid injection. There are several common forms of disinfectant currently employed by the processing industry, including sodium hypochlorite, calcium hypochlorite, chlorine dioxide, ozone and others. It will be readily appreciated by those skilled in the art that each of these disinfectants will require a slightly different means of introduction into the process water stream.

The pH control system 34 is dependent upon the level of pH and the disinfectant employed. For sodium hypochlorite and calcium hypochlorite, the pH control system will preferably involve the introduction of acidification compound at a controlled and monitored rate. The rate of introduction (whether liquid/liquid or gas/liquid) will be monitored and proportionally controlled by the use of a PID or PLC type device to ensure that the pH level is controlled within a tight control band (i.e., for chlorine compounds 6.5–7.0 pH). On line monitoring allows for continuous monitoring of the treatment water by the use of pH probes 36 installed in the piping and distribution system. This assures that the pH level is at the desired "optimum" for the disinfectant employed.

An organic mass removal system 38 (filtration for chiller tanks) incorporates one or more steps designed to remove by physical separation, the organic contamination being constantly introduced to the carcass chiller tank(s) 30. Each animal carcass will have some materials that have not been removed in prior washing. These materials include soluble and insoluble fats, oils, skin, blood products and other contaminants as previously described. The filtration system 38 is designed to remove either all or a major portion of these "filterable solids" in order to reduce the oxidant demand in the chiller tank 30 and thus permit reaching a higher disinfection standard.

As an essential step in the poultry processing system, the chilling process includes vessels into which the poultry carcasses are introduced from the plant's processing lines to reduce temperature of the meat, control bacterial growth through chemical disinfection and hydrate the carcass within the USDA limits of acceptable water content. The process described herein is directed at maintaining the best conditions for chemical disinfection in poultry chiller tanks. As background for such processes, the U.S. poultry industry employs immersion chilling for poultry, carcasses through the use of large volume, stainless steel tanks where the product is mechanically introduced from the processing line(s) after evisceration and inspection.

Figure 3:
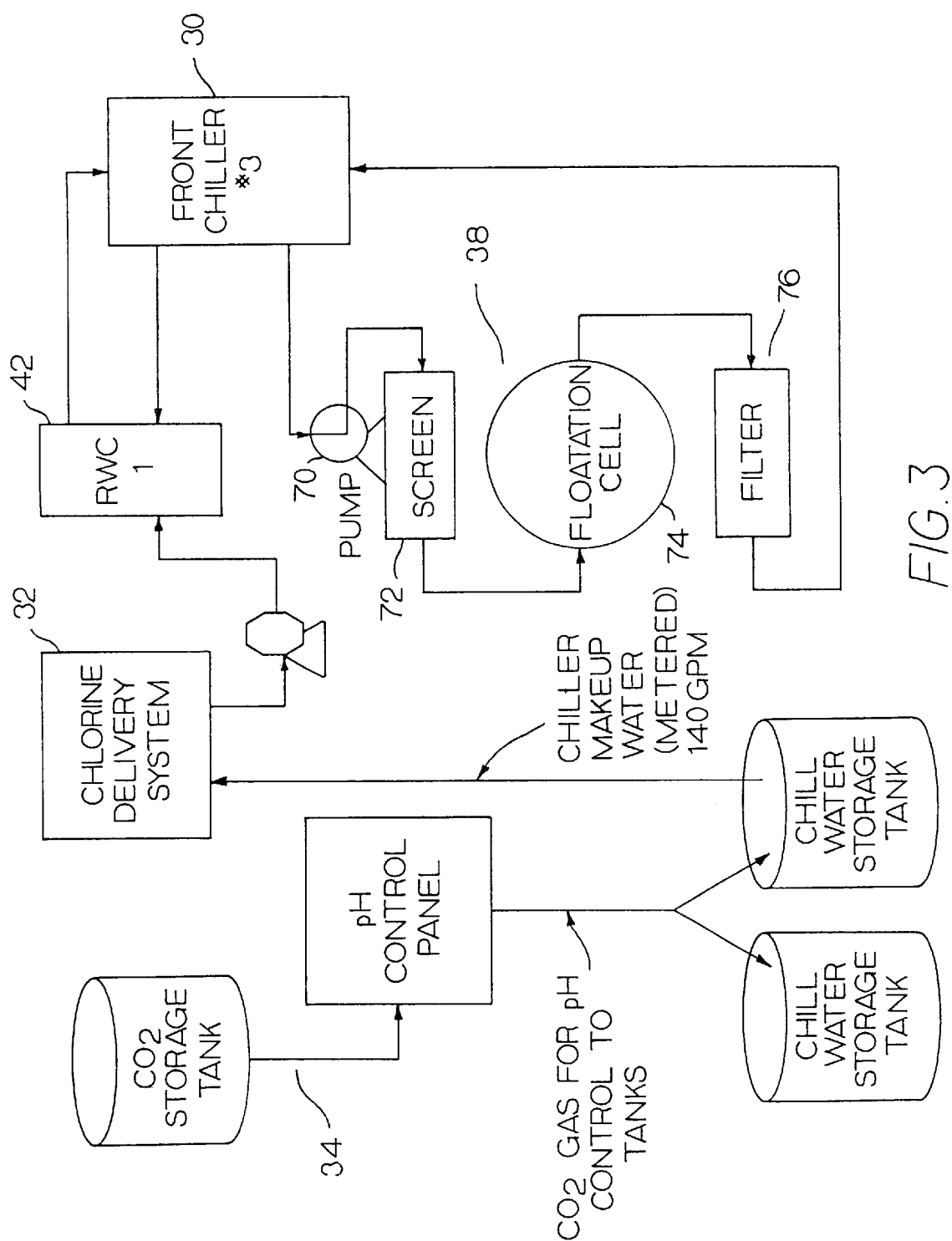
FIG. 3 depicts an alternate view of the chiller treatment system according to the present disclosure.

With reference to FIGS. 2B and 3, such poultry chillers 30 are connected to refrigeration loops, referred to in the industry as a "red water chiller(s)," for the purpose of rejecting heat from chilled water systems. Typically, these red water chiller recirculating systems 42 are closed loop heat exchangers operating with ammonia gas as the refrigerant and electric drive motors to provide the compression/expansion or state change of the refrigerant. The refrigeration chiller 42 typically operates as a closed recirculating loop, where the chiller acts as the heat exchanger to remove heat from the system water in order to maintain the USDA mandated temperature in the chiller tanks.

A mass removal system 38 is designed to continuously remove organic and solids content from the plant's chiller tanks 30 using screening, floatation, filtration and oxidation. The carcasses entering the chiller tanks 30 bring "contaminants" which may be of an organic or inorganic nature and consist of fats, oils, grease, blood products, proteins, lipids and pieces of skin and organs that may have remained after the evisceration. Other inorganic contaminants typically consist of minerals dissolved into the water such as phosphates, nitrogen compounds and other constituents originating in the animal feed or the water used in washing and chilling. The chiller tanks 30 are filled before the first processing shift and are constantly refreshed with potable water during the plant's processing hours (the USDA maintains a requirement of one-half (½) gallon of makeup water per bird). The entering makeup water replaces a similar volume of chiller tank overflow being dispensed from the tank 30. This enables a refreshing of the chiller tank 30 to counteract the cumulative effects of concentration of the contamination brought into the tanks 30 with the carcasses.

It is known that the cumulative effects of constant introduction of the contaminants does negatively impact the effectiveness of carcass disinfection and microbial control. When analyzed for contaminant content, the water from chiller tanks 30 shows that there is a significant level of organic compounds that compete chemically with the microbial content for oxidizer demand. As such, most processing plants have had difficulties in controlling chlorine levels due to the presence of high organic loading.

The carcasses will typically remain in the chiller tanks 30 for between 45 minutes and several hours. The dwell time will be determined by the carcass weight, number of carcasses and efficiency of the chiller system in terms of refrigeration capacity. The controlling factor is the time required to achieve the temperature set by the USDA. The relatively long dwell times should provide an excellent opportunity for microbial control based on the previously described principals of contact time (CT). The limiting factor, however, is overcoming the organic loading resulting from the constant contaminant influx.

As discussed earlier, the process developed according to the present disclosure is directed at providing a continuous, on-line contaminant removal mechanism. The process is effected by the installation of mechanical separation, floatation and filtration devices 38 which are designed to remove organic compounds from the chiller tanks 30. This mass removal of the organic compounds is accompanied by the implementation of enhanced disinfection/microbial control using the most favorable chemistry for chlorination 32, 34, 40. The chemistry, as previously described herein, consists of the combination of pH control 34 and chlorine or other disinfectant injection 32.

The continuous separation, floatation, filtration mechanism 38 for mass removal of the contaminants being introduced into the chilled water tanks 30 is connected to the chiller tank 30 by way of interconnecting piping where a constant volume of water is pumped from the chiller tanks 30, sent to the contaminant removal apparatus, cleansed and returned to the chiller tanks 30. The process is designed to operate continuously. Maintenance of chiller tank water quality is dictated by the disinfection efficiency as measured by the chlorine monitoring devices.

With particular reference to FIG. 3, the chiller tank treatment system process is designed to allow for maximum flexibility of operations based upon the site-specific conditions, load profile and economics. The observed range of chiller system water quality varies significantly across the spectrum of poultry processing plants. In some cases, the operation of the chiller system, together with the size, weight and process rate of birds, will allow a solution that may not require the same mass removal of contaminants as others. A time weighted load factor should be analyzed to assist with the sizing and specification of the components and overall system configuration. This procedure can be accomplished by taking numerous samples of the bulk water in the chiller tanks 30 over a specified period of time. A plot of the contaminant loading will yield a load per hour rate or a load per carcass rate that is important to the sizing and configuration of the treatment solution. A target water quality is established based on the disinfection chemistry and a treatment system is sized to remove the required mass load of contaminants to consistently maintain the target water quality.

The first stage of the system involves pumping water from the chiller tanks 30, by way of a dedicated pump 70 to the treatment system's first stage unit operations. This stage includes a mechanical screening device 72 such as a double drum rotating type, where the influent water is introduced into the internal portion of the device. The double drum screen includes a larger mesh screen as its internal first stage, and a smaller mesh as its external second stage. As the solids are captured on either the internal or external screen surfaces, a traveling, high-pressure water spray nozzle, directed at the surface of the screen, forcibly removes the trapped solids and enhance the screen's ability to maintain flow capacities. The screened water is captured by gravity in a sump located below the screens. The sump is fitted with level sensors to interface with a pump fitted to the sump to allow for automatic operation and to prevent the pump from "dry cycling" when no water is available to pump.

The screened water, now having the preponderance of large solids removed, is pumped to the system's floatation unit 74. This floatation unit 74 could be either of the induced or dissolved air type. Selection of the best method is based on site-specific load characteristics and the targeted mass removal efficiency. Air floatation is well-documented in the literature and operates on well-understood principles of vertical bubble velocity and the ability to attract solids and colloidal materials. Simple skimming and/or overflow removes the floated material. Typical floatation devices are easily adaptable to accept chemical assistance in the form of coagulants, flocculants and other treatment chemicals designed to enhance removal efficiencies. The use of any such chemical assistance would be subject to FDA and USDA regulations and guidelines relating to food quality and safety.

The now screened and floatation treated water is then flowed to the filtration device 76 which removes smaller solids. The selection of the filtration device 76, such as a media filter, will depend upon site-specific conditions. The media filter can use diatomaceous earth as its media and the filter vessel could be of a vacuum leaf, rotating vacuum drum, or pressure leaf design. The smaller solids not removed by the previous stages (screening and floatation) are trapped on the media filter's media matrix which, in the case of diatomaceous earth, has removal efficiencies capable of treating to small micron size particles. The effluent quality from such devices is quite high and is typically below 5 NTU's in turbidity. The treated water is now ready to be transferred back to the chiller tanks 30. At any point along the above identified filtration steps 38, the treated water can be monitored for turbidity via a monitoring device which allows the operator to monitor the system performance. Such a monitoring device can be installed anywhere in-line with alarms, feedback loops or recording devices, which enables total system performance and provides a base for implementing modifications.

It will be readily understood by those skilled in the art that various modifications may be made to the embodiments disclosed herein. Therefore, the above description should not be so construed as limiting, but merely as exemplifications of preferred embodiments. Those skilled in the art will envision other modifications within the scope and spirit of the claims appended hereto.

What is claimed is:

1. A method for improving the effectiveness of a disinfection agent added to an aqueous medium used in the processing of foodstuffs comprising the steps of:
   controlling the pH level of the aqueous medium to a desired range of 6.0 to 8.0 through acidification prior to or concurrent with the addition of the disinfection agent to the aqueous medium.

2. The method for improving the effectiveness of a disinfection agent added to an aqueous medium according to claim 1, wherein said step of adjusting further comprises acidification until the pH level of the aqueous medium is in the range of 6.5 and 7.

3. The method for improving the effectiveness of a disinfection agent added to an aqueous medium according to claim 1, wherein said foodstuffs is poultry and said disinfection agent is chlorine.

4. In a method for processing poultry comprising the steps of scalding, picking, eviscerating, washing, rinsing and chilling said poultry using an aqueous medium, the improvement comprising the steps of:
   controlling the pH level of the aqueous medium to a range of 6 and 8 through acidification prior to or concurrent with the addition of the disinfection agent to the aqueous medium;
   recovering at least a portion of the aqueous medium from the chilling step;
   filtering said recovered aqueous medium to remove particulate matter; and
   reusing said filtered recovered aqueous medium in the chilling step.

5. A method for reducing the level of poultry contamination resulting from the processing of poultry, wherein the processing includes the steps of scalding, picking, eviscerating, washing and rinsing said poultry, the method for reducing the level of poultry contamination comprising the steps of:
   adding a disinfectant to process water used in said processing steps;
   controlling the pH level of said disinfected process water to a range of 6 and 8; and
   using said disinfected process water at each of said processing steps, thereby reducing the level of contamination of the poultry at each of said processing steps.

6. The method for reducing the level of poultry contamination resulting from the processing of poultry according to claim 5, wherein said step of adding a disinfectant to process water is performed prior to any of said processing steps.

7. The method for reducing the level of poultry contamination resulting from the processing of poultry according to claim 5, wherein said disinfectant is selected from the group of chlorine, chloramine, chlorite, chlorine dioxide and ozone.

8. The method for reducing the level of poultry contamination resulting from the processing of poultry according to claim 5, further comprising a step of monitoring and regulating said steps of adding a disinfectant to process water and said step of adjusting the pH level of said disinfected process water.

9. The method for reducing the level of poultry contamination resulting from the processing of poultry according to claim 5, wherein the pH level of said disinfected process water is in the range of 6 and 8.

10. A method for reducing the level of poultry contamination resulting from the processing of poultry, wherein the processing of said poultry includes the steps of scalder, picker, post-pick, washer, rinsing and chilling, the method comprising the steps of:
   recovering water used during at least one of said poultry processing steps;
   treating said recovered water with a disinfectant and controlling the pH of said recovered water to a range between 6 and 8 to reduce microorganisms therein; and
   reintroducing said treated water into at least one heated processing step which uses heated water, whereby the combination of said treated water and said heated water reduces the level of microorganisms within said poultry.

11. The method for reducing the level of poultry contamination according to claim 10, wherein said at least one heated processing step is selected from the group of the scalder step, the picker step and the post-pick step.

12. The method for reducing the level of poultry contamination according to claim 10, wherein said disinfectant is selected from the group of chlorine and ozone.

13. The method for reducing the level of poultry contamination according to claim 10, wherein said step of treating said recovered water with a disinfectant includes ozonating and chlorinating said recovered water.

14. The method for reducing the level of poultry contamination according to claim 10, wherein said disinfectant is selected from the group of chlorine, chloramine, chlorite, chlorine dioxide and ozone.

15. A system for reducing the level of poultry contamination resulting from poultry processing including the steps of scalder, picker, post-pick, washer, rinsing and chilling, the system including a water reuse and disinfection method, the water reuse method comprising the steps of:

recovering water used during at least one of said poultry processing steps;

treating said recovered water with a disinfectant to reduce the level of microorganisms therein; and reintroducing said treated water into at least one of said poultry processing steps which uses heated water;

the disinfection method comprising the steps of:

adding a disinfectant to water used in said poultry processing steps;

controlling the pH level of said disinfected water to a range between 6 and 8; and using said disinfected water in said at least one of said poultry processing steps which uses heated water, whereby the combination of said reuse water, said heated water and said disinfected water in said poultry processing steps reduces the level of microorganisms within said poultry.

* * * * *